(12) United States Patent
Steffan et al.

(10) Patent No.: US 12,350,161 B2
(45) Date of Patent: Jul. 8, 2025

(54) JOINT REPLACEMENT AUGMENTS AND ASSOCIATED INSTRUMENTATION

(71) Applicant: Howmedica Osteonics Corp., Mahwah, NJ (US)

(72) Inventors: Elena Steffan, Sleepy Hollow, NY (US); Peter Tulkis, Paramus, NJ (US); Morgan Kollmeier, Ridgewood, NJ (US); James Crutcher, Jr., Seattle, WA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 367 days.

(21) Appl. No.: 17/846,240

(22) Filed: Jun. 22, 2022

(65) Prior Publication Data

US 2022/0323227 A1    Oct. 13, 2022

Related U.S. Application Data

(63) Continuation of application No. 16/868,711, filed on May 7, 2020, now Pat. No. 11,395,741.

(60) Provisional application No. 62/848,846, filed on May 16, 2019.

(51) Int. Cl.
| | |
|---|---|
| *A61F 2/34* | (2006.01) |
| *A61B 17/16* | (2006.01) |
| *A61B 17/17* | (2006.01) |
| *A61F 2/30* | (2006.01) |
| *A61F 2/46* | (2006.01) |

(52) U.S. Cl.
CPC ............ *A61F 2/34* (2013.01); *A61B 17/1666* (2013.01); *A61B 17/1746* (2013.01); *A61F 2/30749* (2013.01); *A61F 2/4609* (2013.01); *A61F 2002/30736* (2013.01); *A61F 2002/30784* (2013.01); *A61F 2002/3093* (2013.01)

(58) Field of Classification Search
CPC ...... A61F 2/34; A61F 2/4609; A61B 17/1666; A61B 17/1746
See application file for complete search history.

(56) References Cited

U.S. PATENT DOCUMENTS

| | | | |
|---|---|---|---|
| 5,176,711 | A | 1/1993 | Grimes |
| 5,192,329 | A | 3/1993 | Christie et al. |
| 5,326,368 | A | 7/1994 | Collazo |
| 5,919,195 | A | 7/1999 | Wilson et al. |
| 6,162,257 | A | 12/2000 | Gustilo et al. |

(Continued)

FOREIGN PATENT DOCUMENTS

| | | |
|---|---|---|
| DE | 102011050183 A1 | 11/2012 |
| DE | 102012104651 A1 | 12/2013 |

(Continued)

*Primary Examiner* — Brian A Dukert
(74) *Attorney, Agent, or Firm* — Lerner David LLP

(57) ABSTRACT

A joint replacement system that includes an acetabular cup implant that has an outer surface, a drill bit that has a cutting surface, and a guide separately formed from the acetabular cup implant. The guide has a body that defines first and second guide openings each adapted to receive the drill bit. The system also includes void filler prosthesis that has an implant facing surface and first and second portions connected to the implant facing surface. The first and second portions each have an outer surface that has a geometry corresponding to the cutting surface of the drill bit such that the first and second portions can be received in respective openings in a bone formed by the drill bit.

11 Claims, 14 Drawing Sheets

(56) References Cited

U.S. PATENT DOCUMENTS

| | | |
|---|---|---|
| 7,604,667 B2 | 10/2009 | DeSmet et al. |
| 7,670,343 B2 | 3/2010 | Meridew et al. |
| 7,918,896 B2 | 4/2011 | DeSmet et al. |
| 7,985,260 B2 | 7/2011 | Keefer et al. |
| 7,993,408 B2 | 8/2011 | Meridew et al. |
| 8,506,569 B2 | 8/2013 | Keefer et al. |
| 8,568,487 B2 | 8/2013 | Keefer et al. |
| 8,728,168 B2 | 5/2014 | Hanssen et al. |
| 8,828,089 B1 | 9/2014 | Perez et al. |
| 9,060,788 B2 | 6/2015 | Bollinger |
| 9,089,430 B2 | 7/2015 | Pappas et al. |
| 9,192,478 B2 | 11/2015 | Weeden |
| 9,345,576 B2 | 5/2016 | Shea et al. |
| 9,386,993 B2 | 5/2016 | Shea et al. |
| 9,668,873 B2 | 6/2017 | Winslow et al. |
| 9,848,989 B2 | 12/2017 | Shea et al. |
| 9,931,210 B2 | 4/2018 | Anderson et al. |
| 9,993,342 B2 | 6/2018 | Forsell |
| 2008/0021568 A1 | 1/2008 | Tulkis et al. |
| 2009/0204225 A1 | 8/2009 | Meridew et al. |
| 2009/0240256 A1 | 9/2009 | Smith |
| 2009/0326670 A1 | 12/2009 | Keefer et al. |
| 2015/0157462 A1 | 6/2015 | Ek et al. |
| 2016/0193051 A1 | 7/2016 | Budhabhatti et al. |
| 2018/0193152 A1 | 7/2018 | Bauer |
| 2018/0263781 A1 | 9/2018 | Anderson et al. |

FOREIGN PATENT DOCUMENTS

| | | |
|---|---|---|
| JP | 2010012254 A | 1/2010 |
| WO | 2011012892 A1 | 2/2011 |
| WO | 2016086119 A1 | 6/2016 |

JOINT REPLACEMENT AUGMENTS AND ASSOCIATED INSTRUMENTATION

CROSS-REFERENCE TO RELATED APPLICATIONS

This application is a continuation of U.S. patent application Ser. No. 16/868,711, filed on May 7, 2020, which claims the benefit of U.S. Provisional Application No. 62/848,846, filed May 16, 2019, the disclosures of which are incorporated by reference herein.

BACKGROUND OF THE INVENTION

Joint replacement surgery is a common orthopedic procedure for joints such as the shoulder, hip, knee, ankle and wrist. Prior to implanting prosthetic components in a joint of a patient, a surgeon generally has to resect at least a portion of the patient's native bone in order to create a surface and/or recess or void for supporting, accepting or receiving at least a portion of the prosthetic components being implanted. Generally, a surgeon only resects the amount of bone that is needed in order to properly implant the prosthetic components in the joint because once native bone is resected from a joint, it is gone forever. Thus, the surgeon typically attempts to maintain as much of the native structural integrity of the joint as he or she can during the resection process.

However, issues of additional loss of native bone near the joint being replaced are often encountered in revision procedures or in circumstances of trauma or significant disease. With respect to revision procedures, this bone loss is typically due to movement of the primary prosthesis after its initial implantation or even degeneration or further degeneration of the bone, which can form bone defects or bone voids that have unpredictable and non-uniform shapes. In addition, revision procedures often involve the removal of additional bone, which makes maintaining or otherwise restoring the structural integrity often afforded by native bone of great importance.

Thus, when bone defects are observed, it is standard surgical practice to fill or augment those defects as part of the surgical procedure in order to help support the joint prosthesis. The preferred practice is to fill those defects with weight bearing augments or void fillers, typically made of an implant-grade metal such as titanium. However, because the bone defects are typically irregular in shape, some preparation of the defect area is typically required prior to implantation of the augment. However, such preparation is often performed unguided using common surgical instruments, such as ronguers, which are not particularly adapted for contouring the bone to match the augment, thus, requiring a time consuming iterative approach of cutting, evaluating, cutting again and so forth until a reasonable match is achieved. Moreover, it is often the case that more bone is removed than necessary when preparing bone to receive an augment at least because current augments are often larger than the defect they augment. Thus, further improvements are desirable.

SUMMARY OF THE DESCRIPTION

In one aspect of the present disclosure, a method of augmenting a bone defect in proximity to an acetabulum is described as includes: implanting an acetabular cup implant into a bone; after implanting the acetabular cup implant, driving a drill bit into the bone so as to form a first void having a geometry corresponding to that of the drill bit; and inserting a void filler into the void formed by the drill bit such that a portion of the void filler is in a working relationship with the acetabular cup implant and another portion of the void filler is disposed within the void.

Additionally, the working relationship between the void filler and acetabular cup may include one of direct contact between the acetabular cup implant and the void filler or indirect contact between the acetabular cup implant and void filler via an adhesive interposed therebetween. The method may also include drilling the acetabulum prior to implanting the acetabular cup implant. The acetabular cup implant may include a porous outer surface adapted to promote bone ingrowth into its porous structure. The driving step may include driving the drill bit through a first guide aperture of a guide and also driving the drill bit through a second guide aperture of the guide into the bone to form a second void offset from the first void. The inserting step may include inserting the void filler into the first and second voids. The inserting step may include impacting the void filler into the first and second voids in a press-fit manner.

Continuing with this aspect, the method may further include driving first and second bone screws through the void filler and into the bone so as to secure the void filler thereto. The first bone screw may be driven through a screw opening of a first cylindrical boss, and the second bone screw may be driven through a screw opening of a second cylindrical boss. The inserting step may include respectively inserting the first and second cylindrical bosses into the first and second voids. The first and second cylindrical bosses may each include a porous outer surface adapted to promote bone ingrowth into its porous structure.

In a further aspect of the present disclosure, a method of augmenting a bone defect in proximity to an acetabulum, includes: implanting an acetabular cup implant into an acetabulum; engaging the acetabular cup implant with a guide; drilling through the guide into underlying bone with a region of a bone defect to form a void; and while the acetabular cup implant remains in the acetabulum, inserting a portion of a void filler into the void such that a portion of the void filler extends from the void and is positioned within the bone defect and adjacent to the acetabular cup implant.

Additionally, the method may further include drilling the acetabulum prior to implanting the acetabular cup implant. Also, the engaging step may include contacting a convex outer surface of the acetabular cup with a concave surface of the guide. The engaging step may include holding a handle of an instrument, the guide being connected to a distal end of the instrument and the handle being disposed at a proximal end thereof. Further, the drilling step may include inserting a drill bit through a guide opening in the guide.

Continuing with this aspect, the guide opening and drill bit may be cylindrical. The inserting step may include inserting a cylindrical boss of the void filler into the void. The cylindrical boss may have an outer diameter larger than that of the drill bit such that the cylindrical boss of the void filler is inserted into the void in a press-fit manner. The method may also include driving a threaded fastener through the cylindrical boss of the void filler into the bone so as to secure the void filler thereto. The cylindrical boss may have a porous outer surface. Also, engaging the void filler with the acetabular cup implant may include contacting a convex outer surface of the acetabular cup implant with a concave surface of the void filler. Further, contacting the convex outer surface of the acetabular cup implant with the concave surface of the void filler may be performed either directly or indirectly in which an adhesive is interposed between the convex and concave surfaces.

In a yet further aspect of the present disclosure, a method of augmenting a bone defect in proximity to an acetabulum, includes: inserting a first member into an acetabulum; engaging the first member with a second member; drilling through the second member into underlying bone in proximity to the acetabulum to form a first void; drilling through the second member into the underlying bone to form a second void offset from the first void; and inserting a first portion of a void filler into the first void and a second portion of the void filler into the second void.

Additionally, wherein the first and second drilling steps may be performed sequentially. The second member may remain engaged to the first member between the first and second drilling steps. Also, the first member may remain within the acetabulum during the first and second drilling steps. The first and second portions may be inserted into the respective first and second voids in a press-fit manner.

Also, the method may include inserting bone screws through the first and second portions and into the underlying bone. The first member may be an acetabular cup implant. Further, the method may include inserting bone screws through the acetabular cup implant to secure the acetabular cup implant to the acetabulum. The second member may be a guide and the step of engaging the first member with the second member may include contacting a convex outer surface of the first member with a concave surface of the second member. The second member may include a body defining first and second guide apertures and the first and second drilling steps may include drilling through the first and second guide apertures.

Also described is a method of augmenting a bone defect in proximity to an acetabulum, comprising: drilling an acetabulum; drilling first and second voids within a region of a bone defect in proximity to the acetabulum; implanting an acetabular cup implant into the acetabulum; and implanting a unitary void filler into the first and second voids so as to support the acetabular cup implant within the region of the bone defect; and/or Even further described is a joint replacement system is described as comprising: an acetabular cup implant having an outer surface; a drill bit having a cutting surface; a guide separately formed from the acetabular cup implant and having a body defining first and second guide openings each adapted to receive the drill bit; and a void filler prosthesis having an implant facing surface and first and second portions connected to the implant facing surface and each having an outer surface having a geometry corresponding to the cutting surface of the drill bit such that the first and second portions can be received in respective openings in a bone formed by the drill bit; and/or Additionally, wherein the cutting surface of the drill bit may define a cylinder and the outer surface of each of the first and second portions of the void filler prosthesis may be cylindrical. A cross-sectional dimension of each of the first and second portions may be larger than a cross-section dimension of the drill bit so as to create a press-fit arrangement between the first and second portions and the bone when the first and second portions are received in the openings thereof. The implant facing surface may be concave and an upper surface of the void filler prosthesis may intersect the concave surface, the upper surface may define a plane, and the first screw opening may define a longitudinal axis that intersects the plane at a first angle. The first angle may be 90 degrees. The first angle may be also be 60 to 90 degrees. The second screw opening may also define a second longitudinal axis parallel to the first longitudinal axis.

Continuing with this aspect, the guide may have a flange having a concave surface corresponding the outer surface of the acetabular cup implant, the flange may be connected to the body of the guide, the outer surface of the acetabular cup implant may be convex. The void filler prosthesis may include a flange connected to the first and second portions, the flange may have the implant facing surface. The implant facing surface may be concave. The flange of the guide may have a first thickness and the flange of the void filler may have a second thickness, the first thickness may be greater than the second thickness. The void filler prosthesis may include a web connecting the first and second portions and the flange.

In a yet a further aspect of the present disclosure, an acetabular augment is described as comprising: first and second bosses each having an outer surface of revolution; a web portion connecting the first and second bosses; and a flange connected to the first and second bosses via the web, the flange having a concave surface facing away from the first and second bosses.

Additionally, the outer surface of revolution of each of the first and second bosses may have a porous structure adapted to promote bone ingrowth. Also, the first and second bosses may each define a bone screw opening adapted to receive a bone screw therein. Further, the first and second bosses may be connected at a first end thereof by the web and are separated by a gap at a second end thereof. The first boss may define a first longitudinal axis extending in a first plane and the first end of the first boss may be curved in the first plane. The concave surface of the flange may be corrugated. The flange may be a convex surface disposed opposite the concave surface and side surfaces extending between the convex and concave surfaces.

Also, the first and second bosses may include upper and lower ends and the side surfaces of the flange may include upper and lower side surfaces. The lower ends of the first and second bosses may be positioned further from the upper side surface than the lower side surface in a first direction. The outer surface of revolution of first and second bosses may be cylindrical. The outer surface of revolution of first and second bosses may be conical. The proximal end of the acetabular augment may be beveled.

BRIEF DESCRIPTION OF THE DRAWINGS

The features, aspects, and advantages of the present invention will become better understood with regard to the following description, appended claims, and accompanying drawings in which:

DETAILED DESCRIPTION

FIGS. 1A-1D depict an augment or void filler prosthesis 100 according to an embodiment of the present disclosure. As described below, augment 100 is used to fill a defect in bone, particularly an acetabular defect, such as Paprosky classified type 2a and 2b defects, for example. As shown, augment 100 generally includes a flange 110, a web 120, and a plurality of bosses or pegs 122a-b.

Figure 1A:
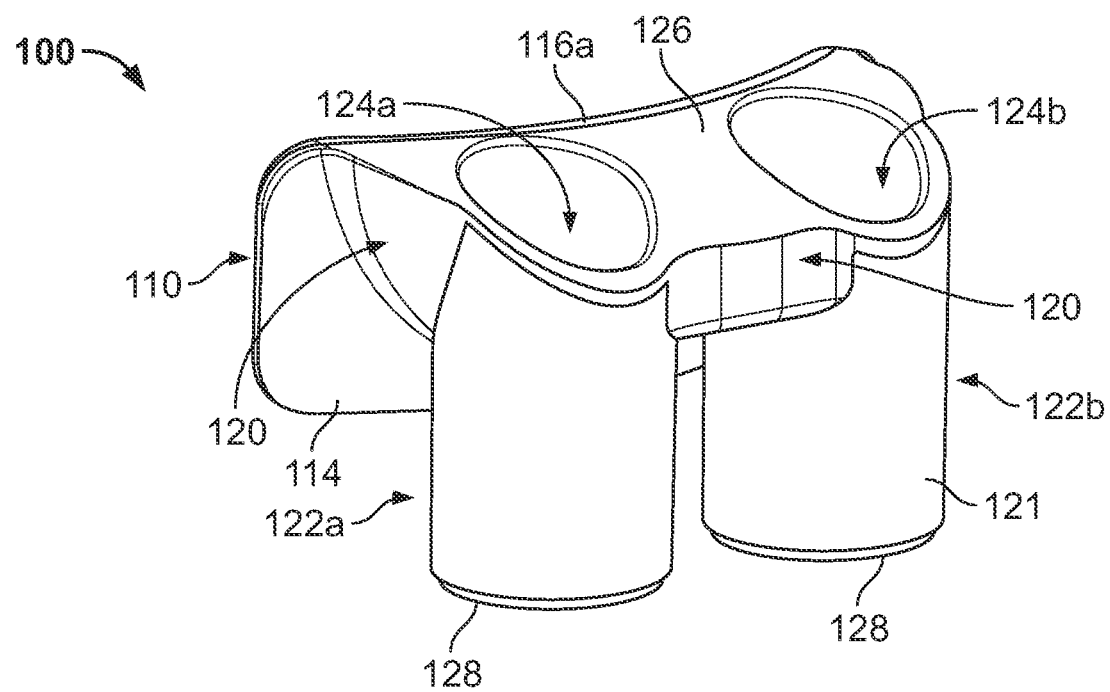
FIG. 1A is a rear perspective view of an augment according to an embodiment of the present disclosure.
Figure 1B:
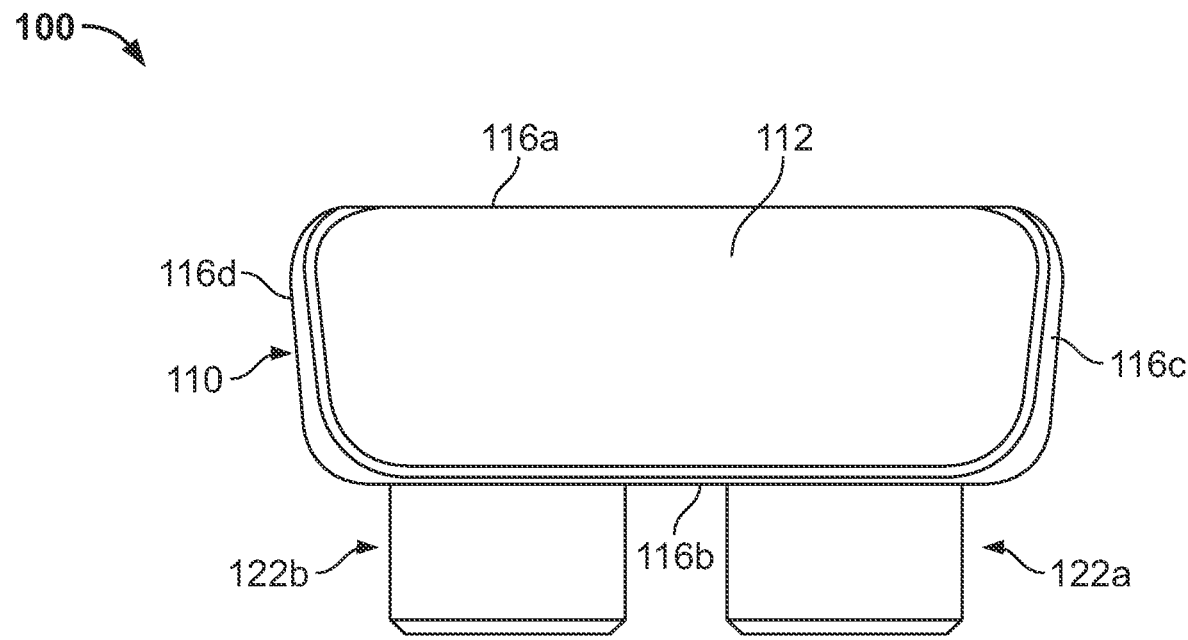
FIG. 1B is a front elevational view of the augment of FIG. 1A.
Figure 1C:
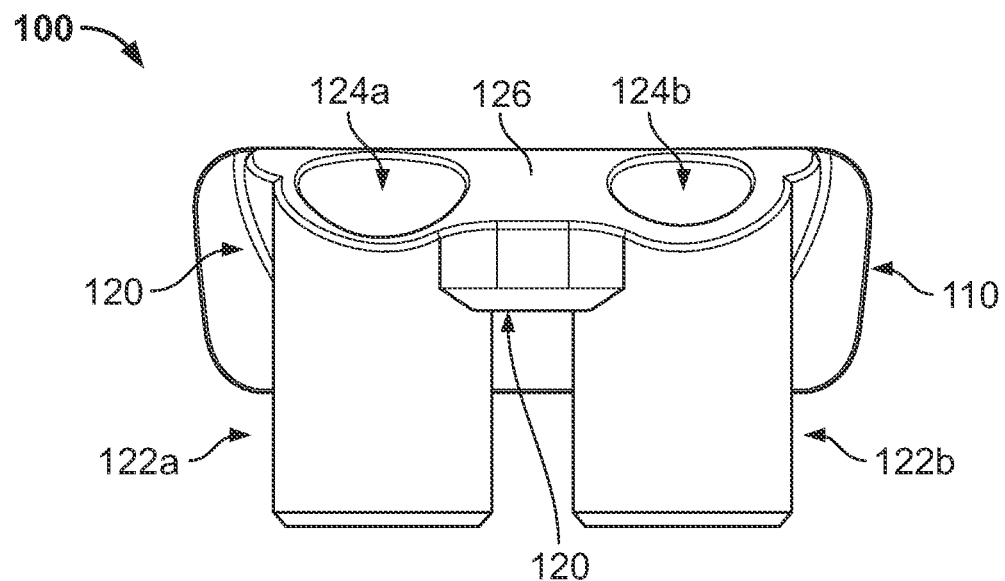
FIG. 1C is a rear elevational view of the augment of FIG. 1A.
Figure 1D:
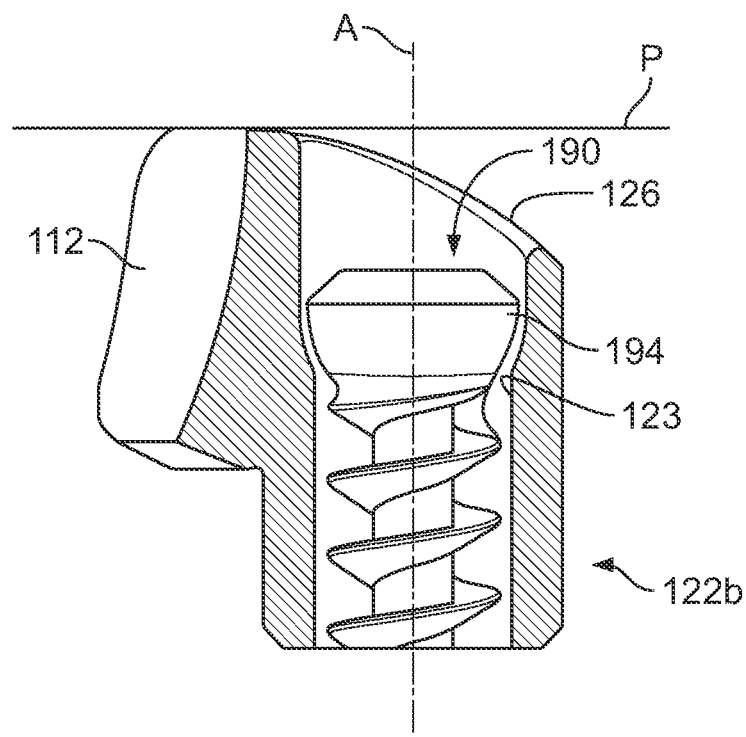
FIG. 1D is a cross-sectional view of the augment of FIG. 1A.

Bosses or sleeves 122 each have an outer surface 121 that is a surface of revolution about a longitudinal axis "A" as shown in FIG. 1D. In the embodiment depicted, outer surface 121 is cylindrical. However, in other embodiments, outer surface 121 may be frustoconical, for example. In other words, bosses 122a-b may be frustoconically shaped. Bosses 122a-b each have screw openings 124a-b extending therethrough. As shown in FIG. 1D, a shoulder 123 is formed on the inside of each screw opening 124a-b so as to interface with a head 194 of a bone screw 190 positioned therein. The embodiment depicted has two bosses 122a-b. However, in other embodiments, augment 100 may include one boss or 3 or more bosses, such as 3 to 5 bosses, for example. Bosses 122a-b are connected to each other via web 120. Web 120 can be connected to bosses 122a-b anywhere along the respective lengths thereof. However, it is preferable that web 120 connects to and extends between bosses 122a-b at a proximal or first end of each boss 122a-b so that a gap is formed therebetween at a distal or second end of bosses 122a-b. This gap allows the distal ends of bosses 122a-b to be inserted into respective bone openings while still being connected to each other as a unitary or monolithic device.

As mentioned above, bosses 122a-b each have a proximal end and a distal end. As shown, the distal end of each boss 122a-b has a flat end surface 128 with a chamfered edge. However, the proximal ends of bosses 122a-b, as well as the web 120 that extends therebetween, are curved or beveled to form a proximal curved surface or bevel 126 of augment 100. More particularly, proximal curved surface 126 is curved in a plane along which axis A of ether boss 122a or 122b extends and that is perpendicular to plane "P," as best illustrated in FIG. 1D. Moreover, proximal surface 126 slopes downwardly toward the distal ends of bosses 122a-b in a direction away from flange 110. Such curvature helps match the anatomy of a bone and helps to reduce soft tissue irritation that overlies augment 100 when implanted. Plane P is a plane defined by an upper side surface 116a of flange 110, as described below.

Flange or abutment plate 110 is connected to bosses 122a-b via web 120. However, in some embodiments, augment 100 may not include a web and instead flange 100 connects bosses 122a-b together to form a monolithic structure. Flange 110 has a concave or implant facing surface 112 and a convex or rear surface 114 opposite concave surface 112. A distance between such surfaces defines a thickness of flange 110. Flange 110 is connected to bosses 122a-b such that concave surface 112 faces away from bosses 122a-b. In addition, flange 110 has side surfaces 116a-d that extend between concave and convex surfaces 112, 114. Side surfaces 116a-d include a proximal or upper side surface 116a, a distal or lower side surface 116b, and lateral side surfaces 116c-d. Concave surface 112 is spherically curved such that it is curved in a first direction extending between upper and lower side surfaces 116a-b and a second direction extending between lateral side surfaces 116c-d. Such curvatures of concave surface 112 correspond to a spherically curved convex outer surface 172 of an acetabular cup implant 170 (see FIG. 4B). In this regard, the radius of curvatures of concave surface 112 generally match that of convex outer surface 172 so that when concave surface 112 contacts convex outer surface 172, concave surface 112 rests against it. Side surfaces 116a-d are generally planar and may be chamfered at their edges to reduce sharp edges. In particular, upper side surface 116 defines plane P, as shown in FIG. 1D. Such side surfaces 116a-d, in some embodiments, may be normal to concave surface 112 at their intersection. In this regard, side surfaces 116a-d may each define a plane that extends toward and intersects a center of curvature of concave surface 112.

A distance between lateral side surfaces 116c-d is generally longer than a distance between upper and lower side surfaces 116a-b. In the embodiment depicted, augment 100 has a low profile such that bosses 122a-b and web 120 do not extend beyond upper side surface 116a. However, bosses 122a-b extend beyond lower side surface 116b, as best shown in FIG. 1B, such that the distal end of bosses 122a-b is positioned further from upper side surface 116a than lower side surface 116b. The low profile nature of augment 100 not only helps prevent impingement and soft tissue irritation, but it facilitates minimal removal of bone. Indeed, augment 100 itself may have an overall footprint smaller than that of the defect it is implanted into. Thus, additional bone surrounding the defect need not be removed to accommodate augment 100.

Augment 100 is made from a biocompatible material such as a biocompatible metal (e.g., titanium, stainless steel, niobium, cobalt chromium, and the like) or a biocompatible polymer (e.g., polyether ether ketone). In addition, some of the surfaces of augment 100 may comprise a porous structure that is adapted to promote bone ingrowth. For example, outer surface 121 of each boss 122a-b preferably includes a porous structure, as shown in FIGS. 1A and 1B. However, the remainder of the surfaces of augment 100 may have a solid structure for added strength. In addition, implant facing surface 112 of flange 110 may be corrugated or otherwise roughened, as shown in FIG. 1B, in order to facilitate adherence of an adhesive, such as bone cement. Such solid and porous structure can be achieved through an additive layer manufacturing ("ALM") process, such as 3D printing, so that no separate connection mechanism is necessary to bring together any of the components of augment 100. In some examples, ALM processes are powder-bed based and involve one or more of selective laser sintering (SLS), selective laser melting (SLM), and electron beam melting (EBM), as disclosed in U.S. Pat. Nos. 7,537,664; 8,728,387; 9,180,010; and 9,456,901 as well as U.S. Patent Publication No. 2006/0147332, each of which is hereby incorporated by reference in their entireties herein. Other methods of ALM, which can be used to form the herein described augments, include stereolithography (SLA), fused deposition modeling (FDM), and continuous liquid interface production (CLIP).

Figure 2A:
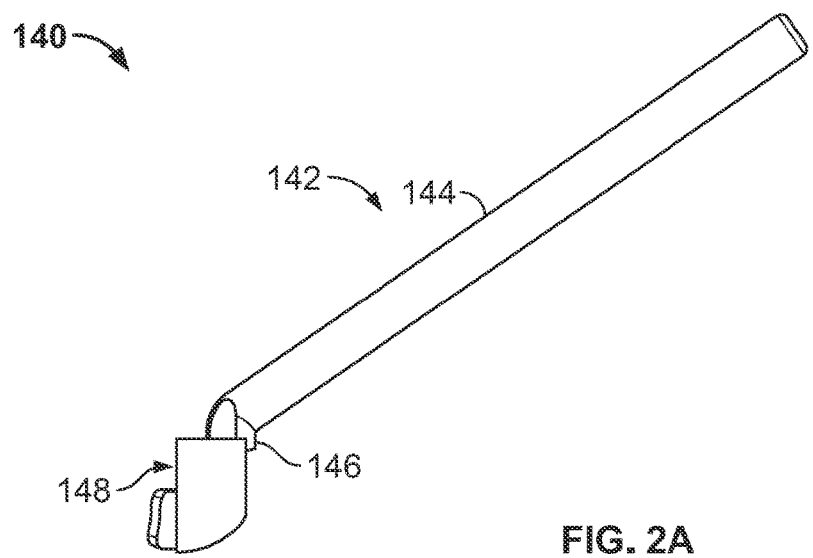
FIG. 2A is a side elevational view of a guide according to an embodiment of the present disclosure.
Figure 2B:
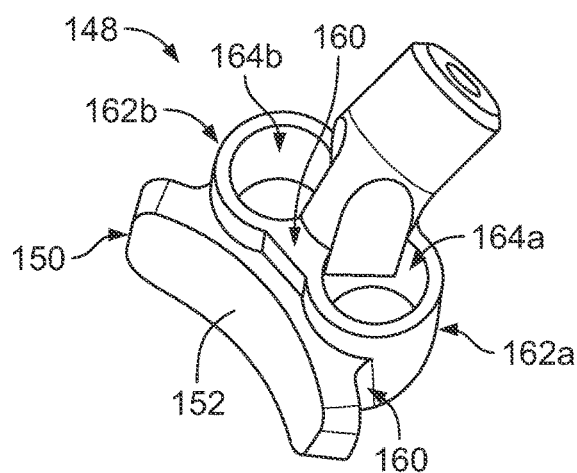
FIG. 2B is a partial upper view of the guide of FIG. 2A.
Figure 2C:
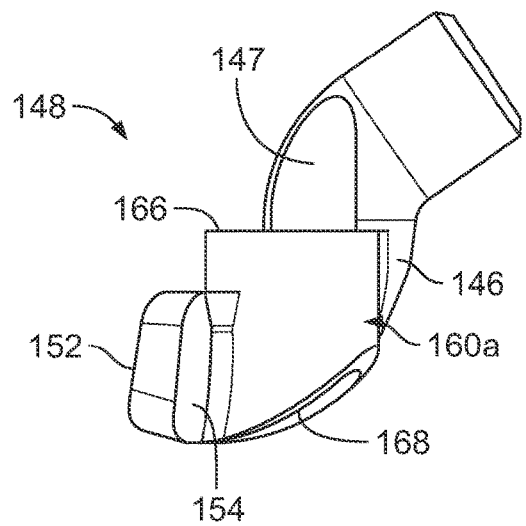
FIG. 2C is a partial side perspective view of the guide of FIG. 2A.
Figure 3A:
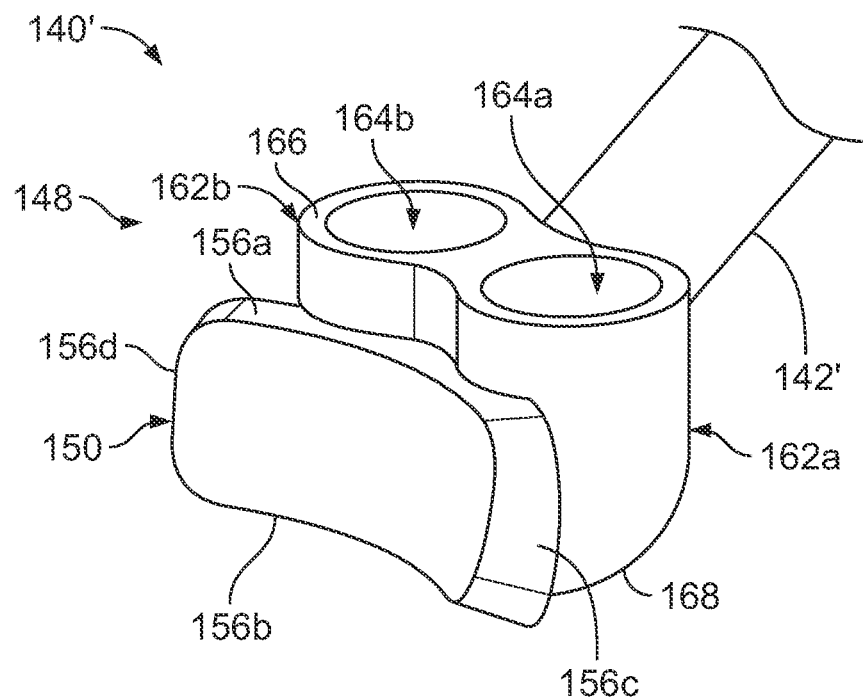
FIG. 3A is a partial front perspective view of a guide according to another embodiment of the present disclosure.
Figure 3B:
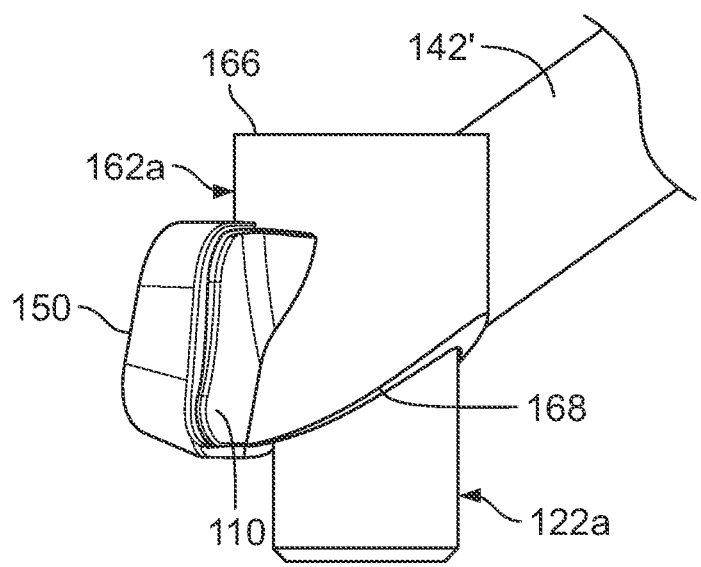
FIG. 3B is a side overlay view of the augment of FIG. 1A and the guide of FIG. 3A.

FIGS. 2A-2C depict a cutter or drill guide 140 according to an embodiment of the present disclosure. Guide 140 includes a handle 142 and a guide body 148 connected at a distal end of the handle 142. FIGS. 3A and 3B depict an alternative cutter/drill guide 140' that also includes a handle 142' and guide body 148. The guide bodies of guides 140 and 140' are functionally the same. Thus, each guide 140, 140' has a guide body designated as guide body 148. In addition, guide body 148 is similarly configured to augment 100. Thus, guide body 148 includes bosses or sleeves 162a-b, a flange 150, and a web 160 connecting bosses 162a-b and flange 150.

However, bosses 162a-b have guide openings 164a-b extending through them that are smooth along their entire length so as to be adapted to receive a cutter/drill bit therethrough. In addition, a cross-sectional dimension of each guide boss 162a-b is larger than a corresponding cross-sectional dimension of each augment boss 122a-b. This is best shown in FIG. 3B in which guide body 148 overlays augment 100. As shown in the overlay, bosses 162a-b are coaxial with bosses 122a-b. Moreover, flange 110 aligns with flange 150. However, flange 150 of guide body 148 has a thickness, as measured between concave and convex surfaces 152, 154 thereof, which is greater than that of flange 110. This difference in thickness, which can be about 1 to 3 mm, creates a standoff distance between an acetabular cup implant and augment 100 so that a sufficient cement mantle can be interposed therebetween, as described further below. However, in other embodiments, flange 150 has the same thickness as that of augment 100 so that no standoff distance is created.

Another difference between guide body 148 and augment 100, which is apparent in the overlay of FIG. 3B, is that bosses 122a-b of augment 100 project distally or lower relative to flange 110 than bosses 162a-b relative to flange 150 of guide body 148. Moreover, bosses 162a-b of guide body 148 project further proximally or upwardly relative to flange 150 than bosses 122a-b relative to flange 110. In this regard, a proximal end or first end of each boss 162a-b is positioned further from a lower side surface 156b of flange 150 than an upper side surface 156a of flange 156b. In addition, a distal end or second end of each boss 162a-b has a curved surface 168. Such curved surface 168 curves in a plane along which a longitudinal axis of each boss 162a-b extends, which creates a clearance so that guide body 148 can be easily seated within a bone defect. In this regard, the configuration of guide body 148 is essentially a flipped configuration of augment 100 with some of the differences noted above.

As mentioned above, guides 140 and 140' each include a handle 142, 142'. Handle 142 of guide 140 has a first portion or proximal portion 144 and a second portion or distal portion 146. Distal portion 146 depends downwardly from proximal portion 144 and connects to web 160 of a proximal surface 166 of guide body 148. Second portion 146 is very short relative to first portion 144. In addition, an enclosed angle formed between them is between 90 and 135 degrees. This configuration allows a drill or cutter to be easily inserted through guide openings 164a-b without interference from handle 142. In addition, second portion 146 has indentations that further provide clearance for a cutter or drill bit. Handle 142', on the other hand, does not include an angled distal portion. Instead, handle 142' is an elongate shaft that connects to a side of guide body 148 between proximal and distal ends of bosses 162a-b and extends away from guide body 148 at an obtuse angle relative to a plane defined by the proximal surface 166 of guide body 148. While handles 142 and 142' are depicted as being integral with guide body 148 so as to form a monolithic structure, it is contemplated that in other embodiments handles 142 and 142' may be separate to guide body 148 and connectable thereto. In this regard, handles 142 and 142' may be universal handles that can connect to a variety of guide bodies 148, such as those that are of different sizes.

Augment 100 and guide 140 or 140' may be included in a system or kit that also includes a cutter/drill bit 180 and an acetabular cup implant 170, as shown in FIGS. 4A-E. Moreover such a kit may also include a plurality of augments 100, guides 140/140', acetabular cup implants 170, and drill bits 180. In this regard, each acetabular cup implant 170 in the kit may be of a different size so that the operator can appropriately fit implant 170 to the patient. In addition, the augments 100 of the kit may differ in size in order to address differently sized defects. In this regard, the larger augments in the kit may have bosses 122a-b positioned further apart (or more than two bosses) and flanges with larger areas in order to fill larger defects than the smaller augments of the kit that address smaller defects. In addition, at least one guide 140/140' is provided for each size augment 100. As such, each guide in the kit has a guide body 148 configured to prepare a bone for an associated augment 100. In other kit embodiments two guides 140/140' may be provided for each augment 100. For example, a first guide 140/140' for a particular sized augment 100 may be configured to provide a standoff distance for such augment 100, as mentioned above, so that such augment 100 can be cemented to the cup implant 170, and a second guide 140/140' may be provided that does not create a standoff distance. In other words, the first guide 140/140' may have a thicker flange than that of the second guide in order to create space for bone cement. In an even further embodiment, the kit may include one universal handle that is connectable to the plurality of differing guide bodies 148 within the kit mentioned above.

Figure 4A:
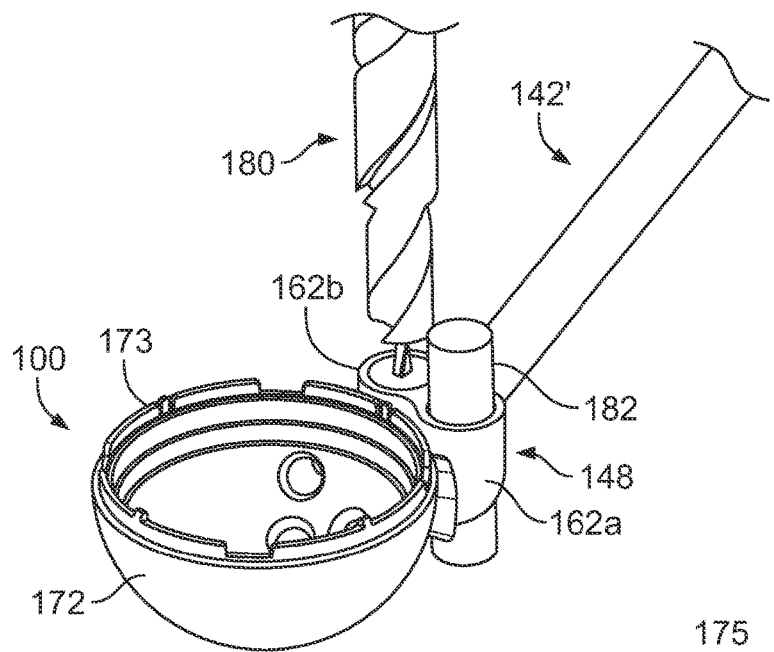
FIGS. 4A-4E illustrate a method of operation.

FIGS. 4A-4E illustrate a method implanting an acetabular cup implant and augmenting a bone defect proximate to an acetabulum to support the implant. In the method, an operator gains access to the acetabulum via a standard incision, retraction of soft tissue, and dislocation of the native hip joint. The acetabulum is reamed using a standard spherical reamer (not shown) to create a surface suitable for an acetabular cup implant 170. Thereafter, the acetabular cup implant 170 is implanted into the acetabulum. The acetabular cup implant 170, as shown, has a spherically convex outer surface 172 and concave inner surface 175 that are joined together by a rim 173. Convex outer surface 172 may include a porous structure, such as for when acetabular cup implant 170 is press-fit into the acetabulum. However, acetabular cup implant 170 may have a non-porous outer surface and may be instead be cemented to the acetabulum. Once the acetabular cup implant 170 is implanted into the acetabulum, the operator assesses bone defects about the implant to determine where augmentation is required.

Where a defect is identified, operator places an appropriate size guide body 148 of guide into the defect such that concave surface 112 of flange 110 engages convex outer surface 172 of implant 170. Multiple guide bodies 148 of different size may be tried until the appropriate size is determined. A cutter or drill bit 180 is driven through first guide opening 164a-b into the underlying bone to form a first bone opening or void. Drill bit 180 may be disconnected from the drill and left partially within the first bone opening in order to prevent inadvertent movement of guide body 148. Alternatively, a peg or pin 182 may be used for the same purpose, as shown in FIG. 4A. The drill bit 180, or a second drill bit, may then be driven through second guide opening 164a into the underlying bone to form a second bone opening or void. Guide body 148 is then removed from the defect.

Figure 4B:
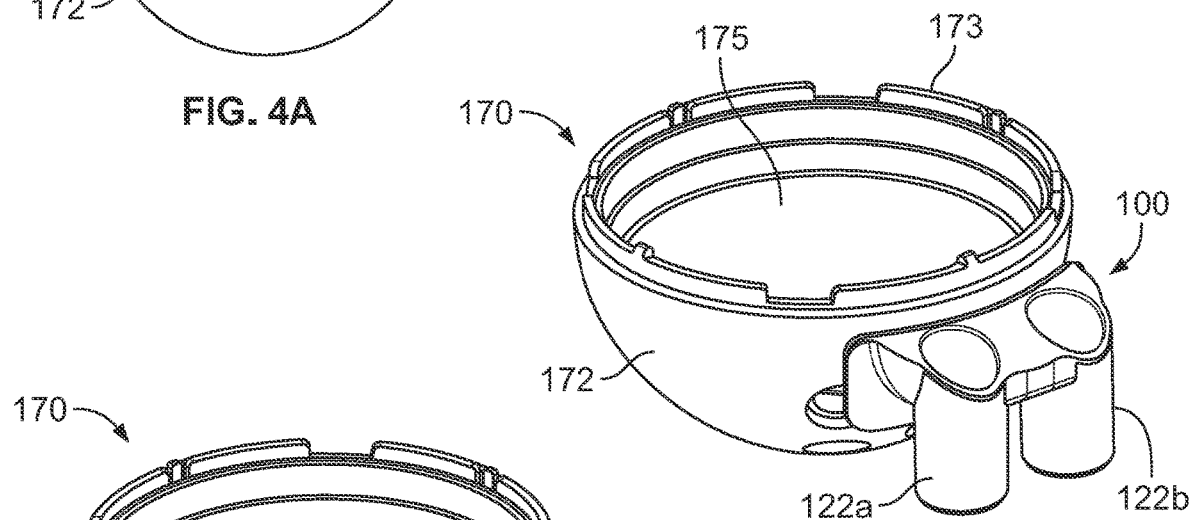
Figure 4C:
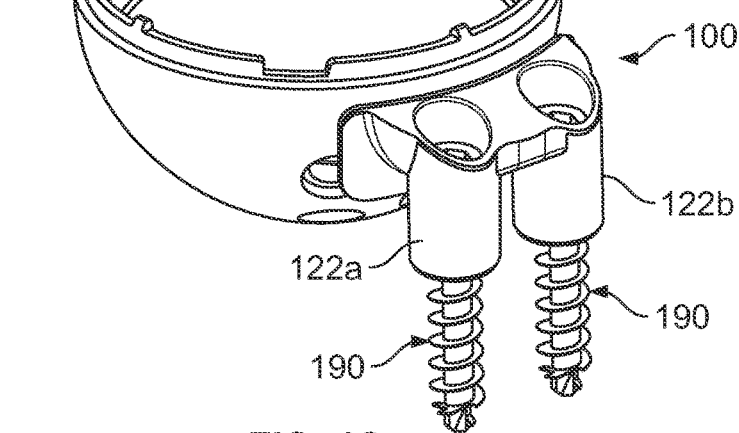

Augment 100 is then inserted into the defect such that first boss 122a is positioned within the first bone opening and second boss 122b is positioned in the second bone opening, as illustrated in FIG. 4B. Drill bit 180 has an outer geometry that matches the geometry of each boss 122a-b of augment 100. Thus, each boss 122a-b has a geometry that matches the respective bone openings formed by drill bit 180. However, bosses 122a-b may have a slightly larger cross-sectional dimension than drill bit 180 such that inserting first and second bosses 122a-b into the first and second bone voids is done in a press-fit manner, such as by impacting augment 100 into the bone. Once augment 100 is fully seated, bone screws 190a-b are driven into the bone through respective first and second bone screw openings 164a-b to further secure augment 100 to the bone, as shown in FIG. 4C.

Figure 4D:
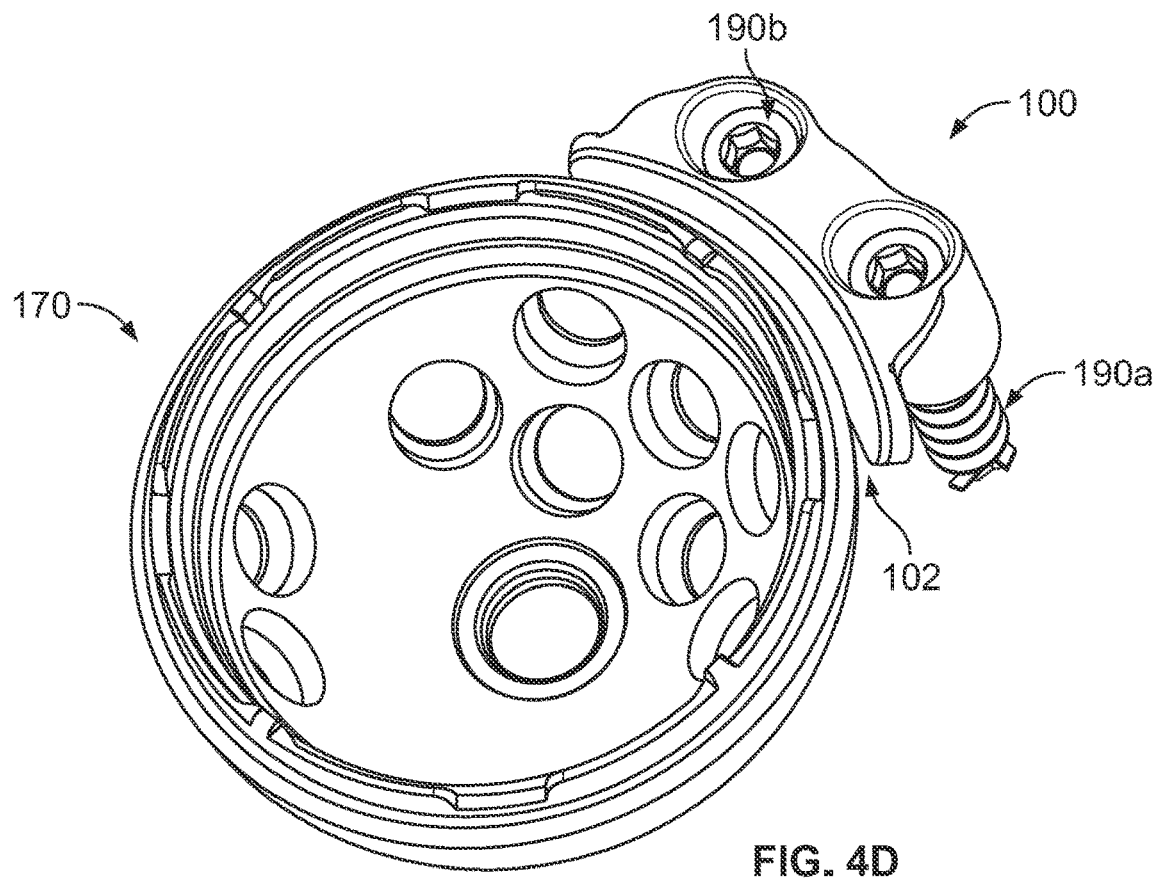

In this configuration, flange 110 may directly contact outer surface 172 of implant 170 in the same manner and at the same location as guide 100 did while the first and second bone openings were formed. This may be achieved where the flange thickness of augment 100 is the same or similar as that of guide body 148. However, in other embodiments, flange 110 may indirectly contact outer surface 172 of implant 170. This may be achieved where the flange thickness of augment 170 is less than that of guide body 148, as described above. In this regard, when augment 100 is implanted, a gap is formed between augment 100 and acetabular cup implant 170, as best shown in FIG. 4D. However, adhesive, such a bone cement, may be disposed within such gap by applying the adhesive to flange 110 prior to insertion of augment 100 into the defect. Alternatively, an operator may deposit an adhesive between acetabular cup implant 170 and augment 100 to connect the same after augment 100 is implanted into the defect. Thus, augment 100 indirectly engages implant 170 via adhesive interposed therebetween. Thus, when augment 100 directly or indirectly engages acetabular implant 170, augment 100 provides support for implant 170 in a region of a bone defect.

Figure 4E:
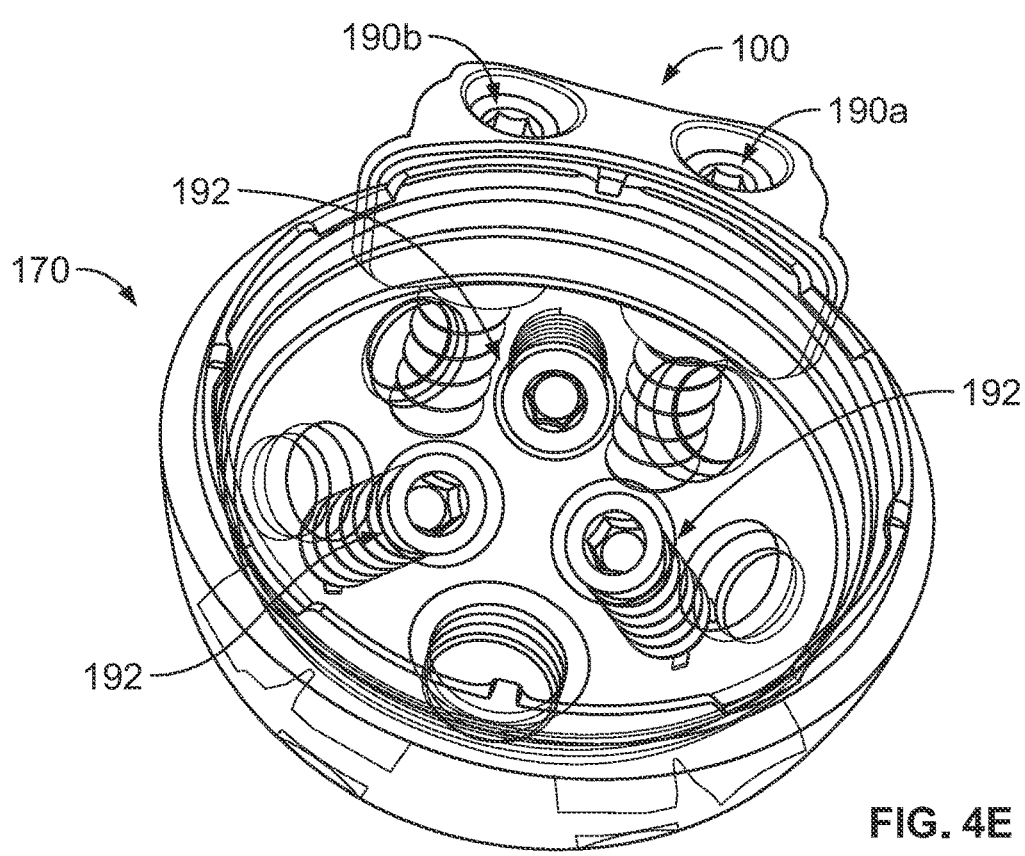
Figure 5A:
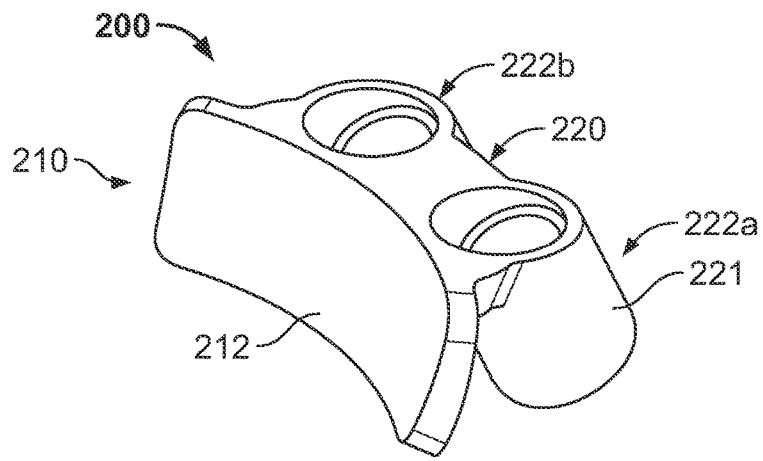
FIG. 5A is a perspective view an augment according to another embodiment of the present disclosure.
Figure 5B:
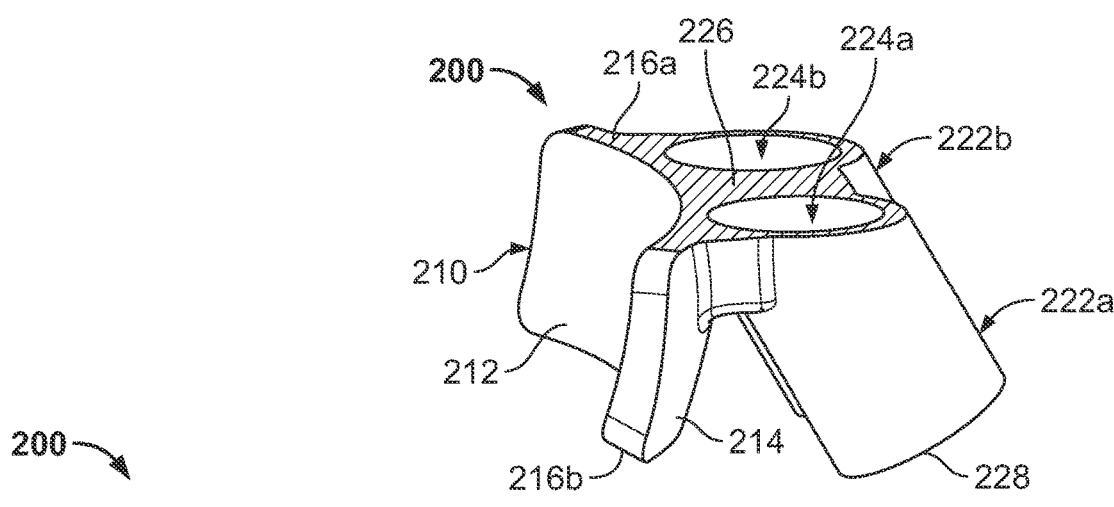
FIG. 5B is a side perspective view of the augment of FIG. 5A.
Figure 5C:
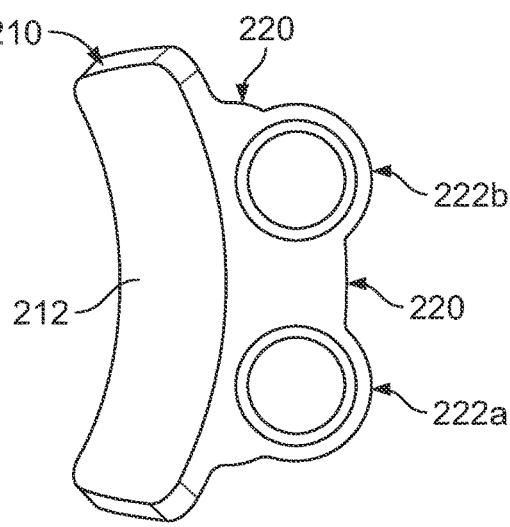
FIG. 5C is a top perspective view of the augment of FIG. 5A.
Figure 5D:
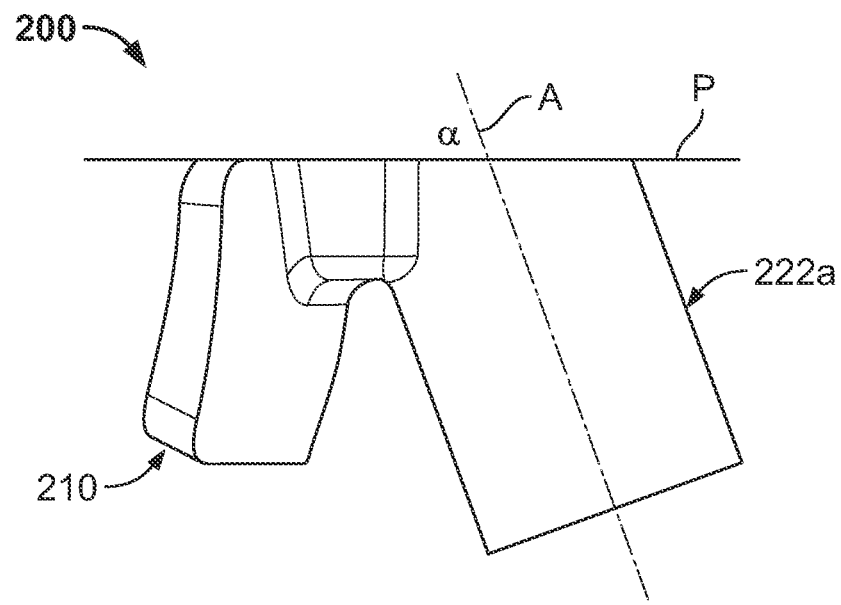
FIG. 5D is a side elevational view of the augment of FIG. 5A.

As shown in FIG. 4E, bone screws 192 may then be inserted through corresponding openings within acetabular cup implant 170 into the acetabulum to further secure implant 170 therein. However, such screws 192 can also be inserted prior to implantation of augment 100. The spacing between first and second bone screw openings 124a-b of augment 100 and, consequently, bone screws 190a-b may be such as to allow a bone screw 192 of acetabular cup implant 170 to be inserted into the bone so that a threaded shank thereof extends between first and second bone screws 190a-b, as shown in FIG. 4E.

FIGS. 5A-5D depict an augment 200 according to another embodiment of the present disclosure. For ease of review, like elements are accorded like reference numerals to that of augment 100, but within the 200-series of numbers. Augment 200 is similar to augment 100 in that it includes a flange 210, bosses 222a-b, and a web 220 connecting flange 210 and bosses 222a-b to form a monolithic structure. Moreover, flange 210 includes a concave surface 212 that corresponds to a convex outer surface of an acetabular cup implant, such as implant 170 previously described. In addition, bosses 222a-b each have an outer surface 221 that is a surface of revolution about an axis A and each define a bone screw opening 22a-b that extends therethrough.

Figure 6:
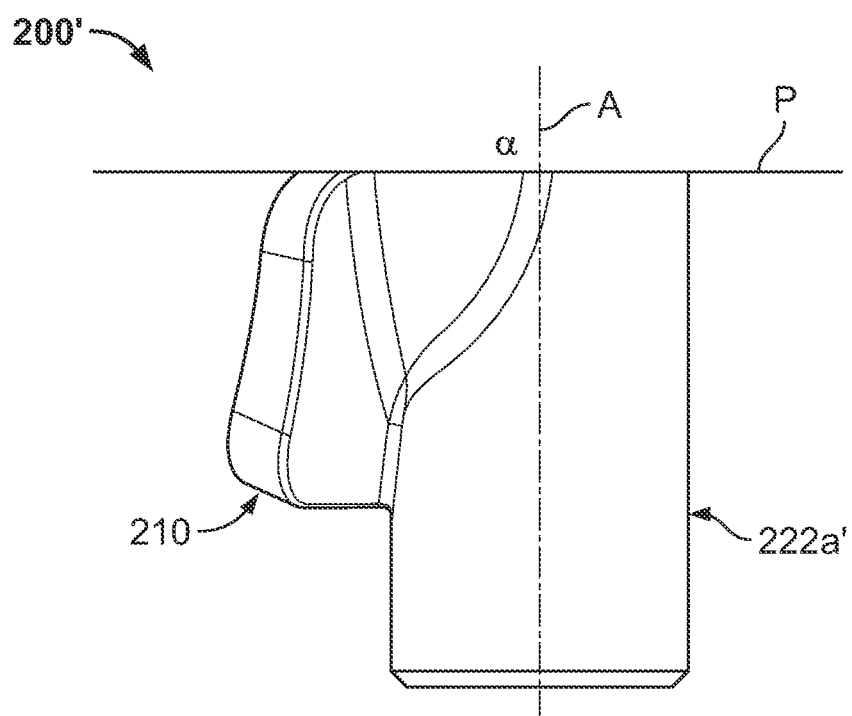
FIG. 6 is a side elevational view an augment according to a further embodiment of the present disclosure.

However, augment 200 differs from augment 100 in that both ends of bosses 222a-b define planar surfaces 226, 228, whereas one end of each boss 122a-b is curved. In this regard, upper side surface 216a of flange 210 is coplanar with proximal surface 226 of web 220 and bosses 222a-b. Moreover, the longitudinal axis A of each boss 222a-b has a different orientation than that of augment 100. In this regard, each axis A is oriented at an oblique angle relative to plane P. As mentioned above, plane P is a plane that is defined by an upper side surface 216a of flange 210. In the embodiment depicted, the enclosed angle α between plane P and axis A may be about 60 to 70 degrees. However, such angle can be greater than 70 degrees, such as 70 to 90 degrees. FIG. 6 depicts such an augment 200'. More particularly, angle α of augment 200' is 90 degrees. This is the same angle of intersection between axis A and plane P of augment 100 shown in FIG. 1D. The range of angle α mentioned above allows the respective bosses of augments 100, 200, and 200' to be inserted into the bone without being obstructed by a rim of an acetabular implant so that bone screws can be easily inserted therein. However, one advantage to a tilt angle α that nears 90 degrees, such as that of augment 200' shown in FIG. 6, is that the augment can be inserted into the bone after implantation of implant 170, whereas a tilt angle α that is more like that in augment 200 of FIG. 5D may require the augment to be implanted prior to implantation of implant 170. In other words, augments 200 and 200' are inserted into the bone along a trajectory defined by axes A. However, the more the tilt angle α diverges from 90 degrees relative to plane P, the more likely the trajectory of insertion would be impeded by an already implanted implant 170.

While augments 100, 200, and 200' include bosses that have parallel longitudinal axes A, it is contemplated that some augment embodiments may include a first boss that has a different orientation relative to a second boss such that bone screws received therein enter into the bone at different angles. Such a configuration may help resist force vectors orientated at a multitude of angles. In this regard, a corresponding guide would have bosses similarly constructed so as to assist in forming bone openings capable of receiving such an augment embodiment.

Figure 7A:
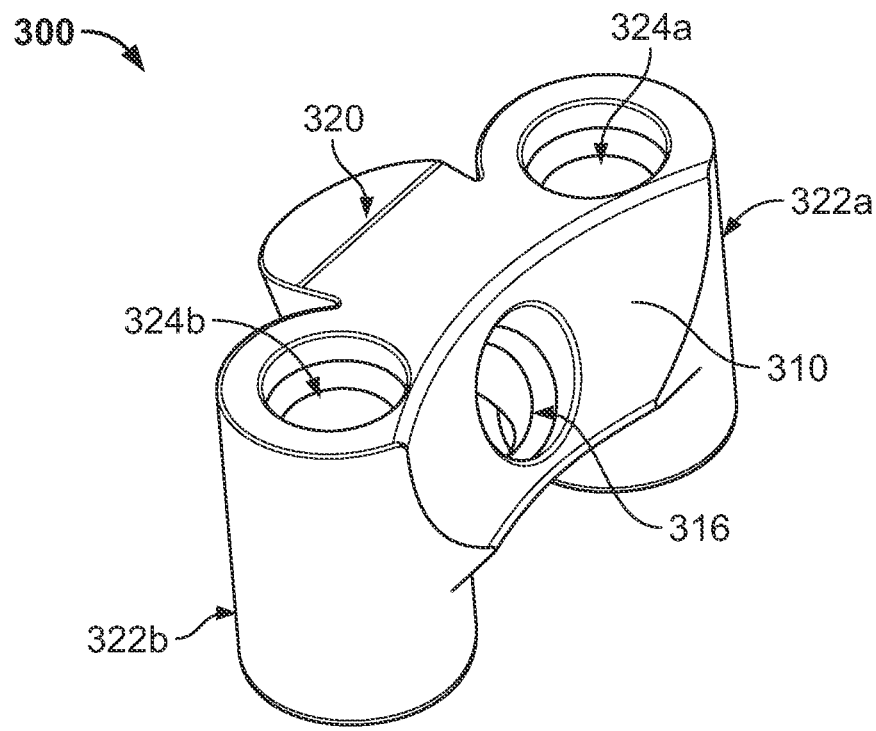
FIG. 7A is a front perspective view of an augment according to an even further embodiment of the present disclosure.
Figure 7B:
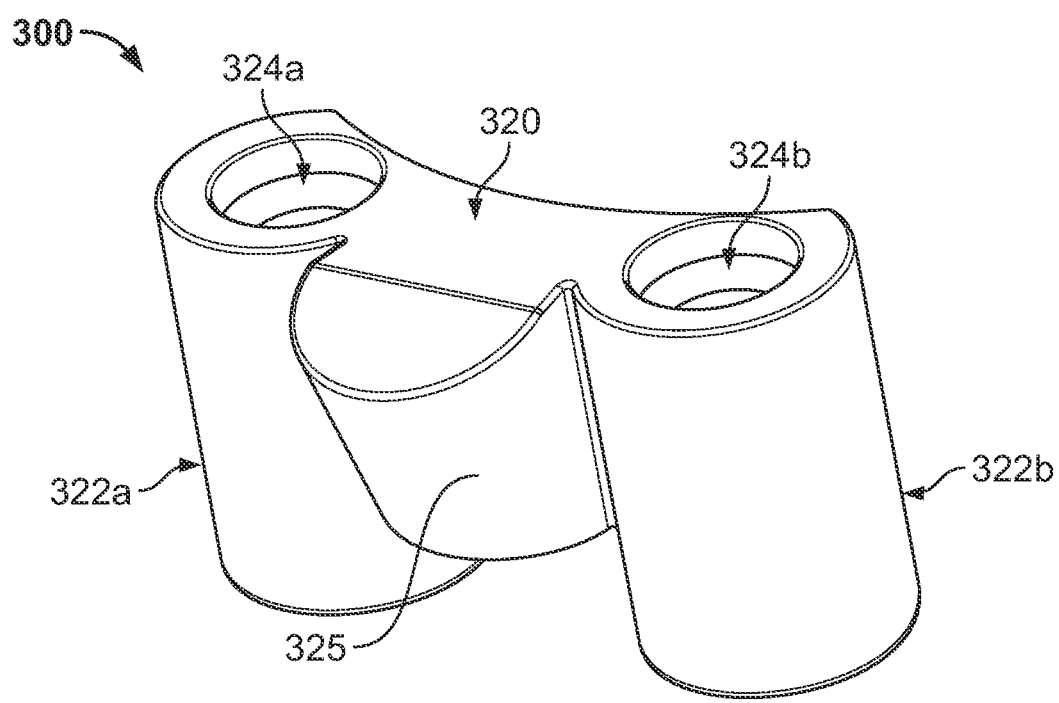
FIG. 7B is a rear perspective view of the augment of FIG. 7A.

FIGS. 7A and 7B depict an augment 300 according to yet another embodiment of the present disclosure. Augment 300 is similar to augment 100 in that it includes a plurality of bosses 322a-b and a web 320 extending therebetween. However, augment 300 differs in that it does not include a flange and instead has a concave surface 310 indented into bosses 322a-b and web 320. In addition, augment 300 includes an additional bone screw opening 316 extending at an angle through concave surface 310 and web 320. Where such bone screw opening 316 is utilized, augment 300 is implanted prior to implantation of the cup implant so that opening 316 is not obscured. Web 320 also includes a conically shaped protrusion 325 that is positioned opposite concave surface 310. An additional drilling operation may be performed to accommodate protrusion 325. In this regard, a guide associated with augment 300 may have a guide body with three guide openings rather than two. Such protrusion 325 may help wedge augment 300 into a defect to further secure augment 300 into the bone.

Figure 8A:
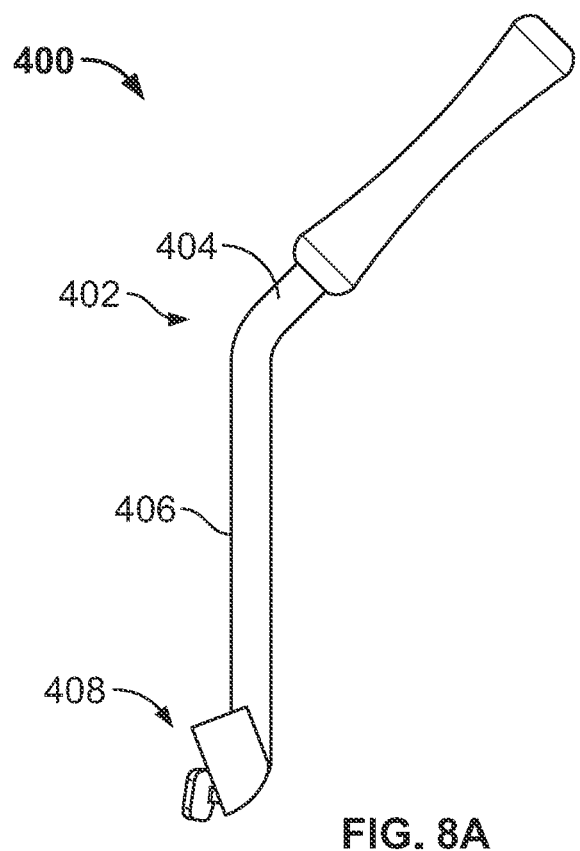
FIG. 8A is a side elevational view of a guide according to a further embodiment of the present disclosure.
Figure 8B:
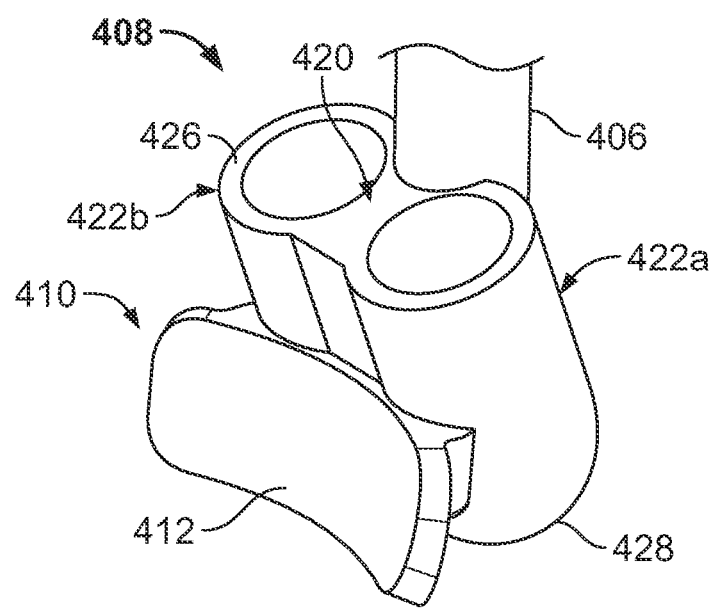
FIG. 8B is a partial top view of the guide of FIG. 8A.
Figure 8C:
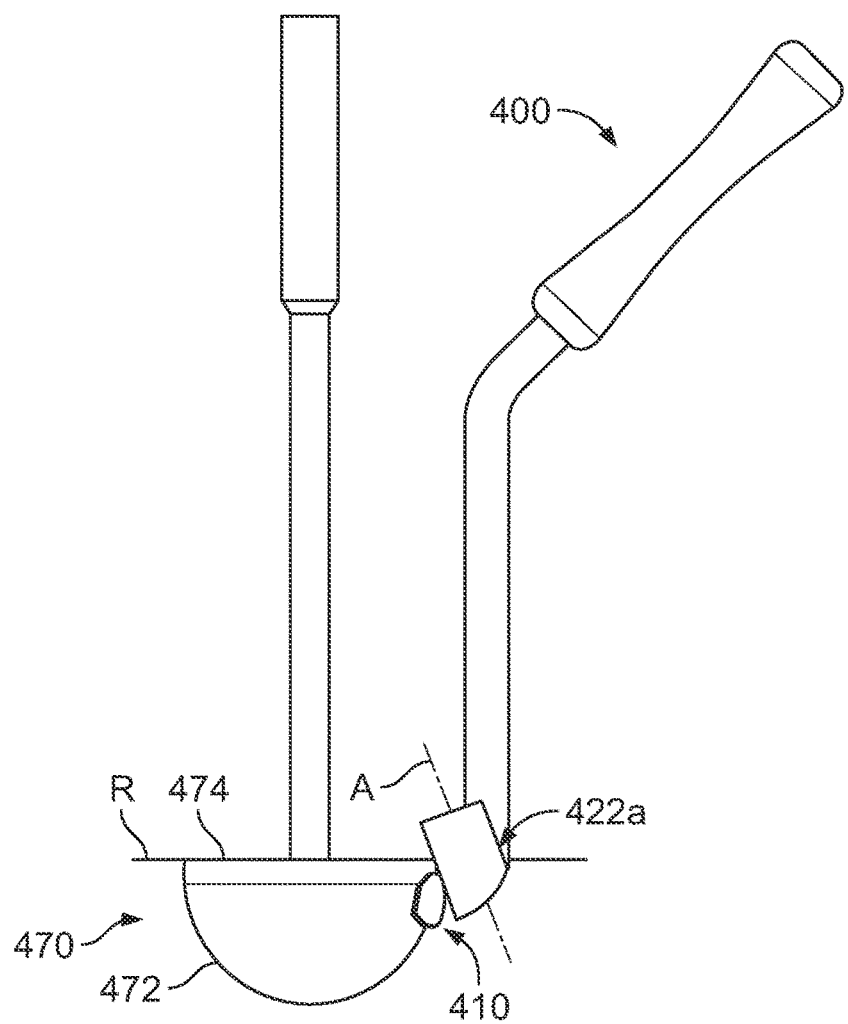
FIG. 8C is a side elevational view of the guide of FIG. 8A in conjunction with an acetabular cup implant.
Figure 8D:
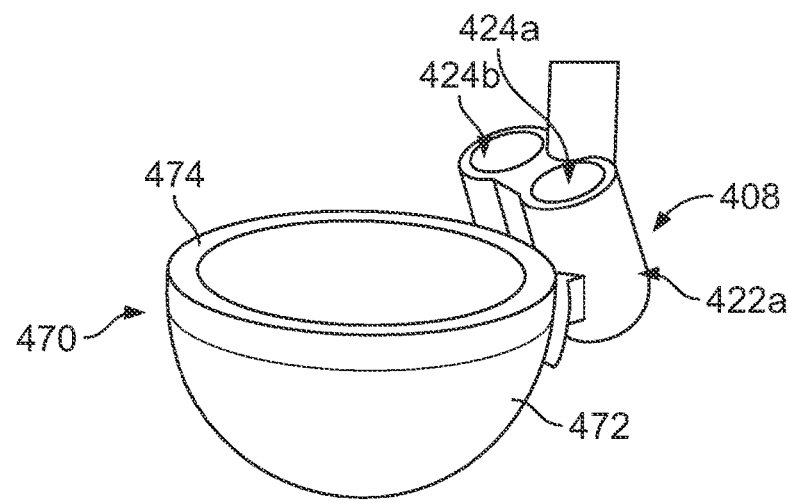
FIG. 8D is an enhanced partial perspective view of FIG. 8C.

FIGS. 8A-8D depict a cutter/drill guide 400 according to a further embodiment of the present disclosure. Drill guide 400 is similar to guide 140 in that it includes a handle 402 and a guide body 408. Guide body 408 is similar to guide body 148 in that it includes bosses 422a-b, a flange 412, and a web 420 connecting the bosses 422a-b and flange 420. However, guide body 408 is configured for use with augments that have angled bosses, such as augment 200, as guide body 408 itself has angled bosses 422a-b. In this regard, when guide 408 contacts an outer surface 472 of an acetabular cup implant 470, guide openings 424a-b are oriented at an oblique angle relative to a plane R defined by a rim 474 of acetabular cup implant 470, as best shown in FIG. 8D. Such oblique angle is influenced by angle α of the corresponding augment. Thus, the angle α helps ensure clearance between bosses 422a-b and rim 474. As can be seen in FIGS. 8D and 8E, if the angle α were very shallow, then bosses 422a-b could impinge on rim 474 thereby preventing flange 410 from contacting implant 470. Handle 402 is also similar to that of guide 140 in that it includes first and second portions 404, 406. However, second portion 406 is longer than first portion and connects to guide body 408 at its side.

Figure 9A:
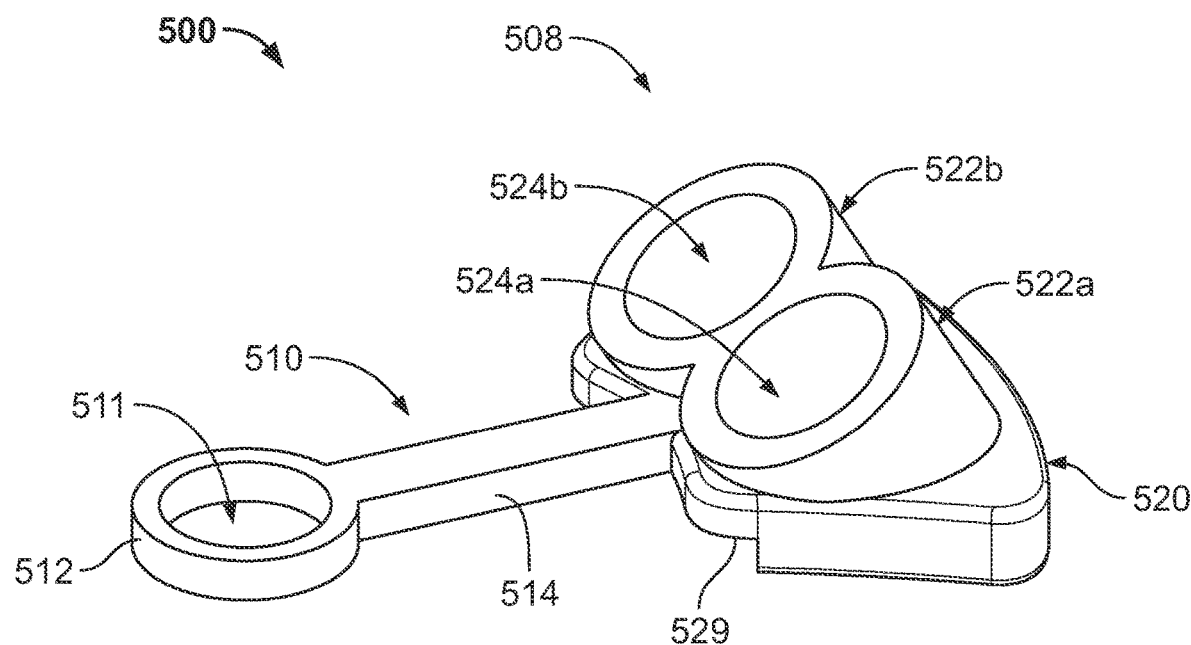
FIG. 9A is a perspective view of a guide according to yet another embodiment of the present disclosure.
Figure 9B:
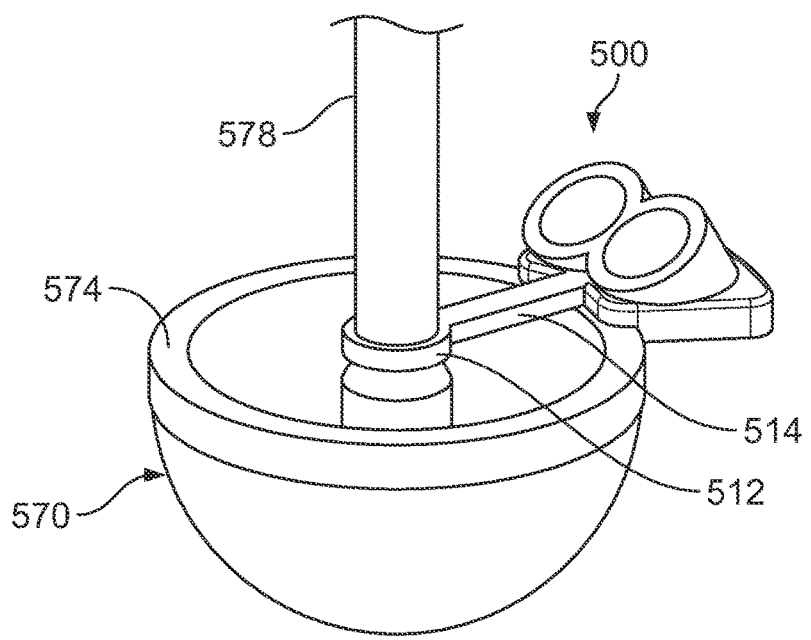
FIG. 9B is a perspective view of the guide of FIG. 9A.

FIG. 9A depicts a cutter or drill guide 500 according to an even further embodiment of the present disclosure. Guide 500 is similar to guide 140 in that it includes a body 508 that is comprised of a plurality of bosses 522a-b for guiding a drill bit, such as drill bit 180, and a web 520 connecting bosses 522a-b. However, drill guide 500 does not include a handle. Instead, guide 500 includes a leash 510 that has a collar 512 and an elongate member 514 extending from collar 510. Collar 512 has an opening 511 that is configured to receive an inserter shaft 578 of an acetabular cup implant 570, as shown in FIG. 9B. In addition, drill guide body 508 has a recess 529 configured to receive a rim 574 of implant 570 so that body 508 sits at least partially on rim 574 of acetabular cup 570 during use. In this regard, recess 529 is curved so that when rim 574 is received by recess 529, a portion of web 520 conforms to the curvature of implant 570, as best shown in FIG. 9B.

In use, an acetabular cup implant 570 is inserted into an acetabulum via an inserter shaft 578 connected to acetabular cup implant 570. Drill guide 508 is attached to inserter shaft 578 either before or after implantation of acetabular cup implant 570 by sliding collar 512 over shaft. The length of leash 514 is correspondent to the particular size of implant 570 so that guide body 508, as tethered by leash 510, is positioned at the appropriate distance from inserter shaft 578 such that guide body 508 rests on rim 574. At this point, guide body 508 can be rotated about inserter shaft 578 in order to align guide openings 524a-b with a bone defect in proximity to the acetabulum. A drill bit can then be driven through guide openings 524a-b to form bone openings for receipt of one of the aforementioned augments.

Figure 10A:
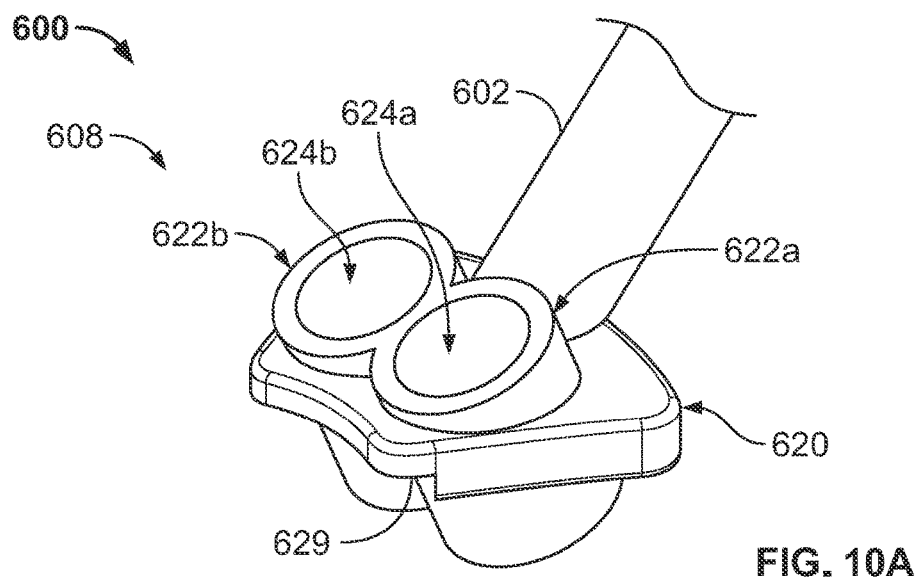
FIG. 10A is a perspective view of a guide according to a still further embodiment of the present disclosure.
Figure 10B:
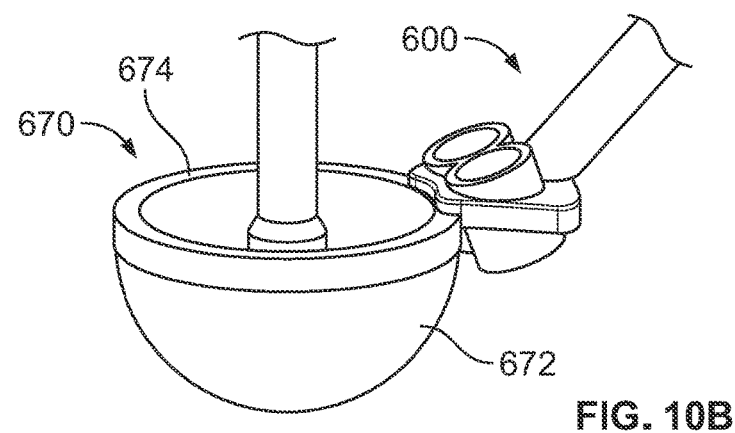
FIG. 10B is a perspective view of the guide of FIG. 10A.

FIGS. 10A and 10B depict a cutter or drill guide 600 according to yet another embodiment of the present disclosure. Guide 600 includes a guide body 608 and a handle 602. Handle 602 is similar to handle 142' in that it connects to guide body 608 at a side thereof and extends outwardly therefrom at a shallow angle to avoid obstructing a clear path of a drill bit to guide openings 624a-b. Guide body 608 is similar to guide body 508 in that it is configured to sit at least partially on a rim 674 of an acetabular cup implant 670, as shown in FIG. 10B, and includes a plurality of bosses 622a-b for guiding a drill bit, such as drill bit 180, and a web 620 connecting the bosses 624a-b. Thus, guide 600 generally differs from guide 500 in that instead of utilizing leash 514 to position and retain guide 500 relative to an acetabular cup implant 570, guide 600 includes handle 602, which may be manipulated by the operator to position and hold guide body 608 in place on rim 674 and against outer surface 672 of acetabular cup implant 670.

Figure 11:
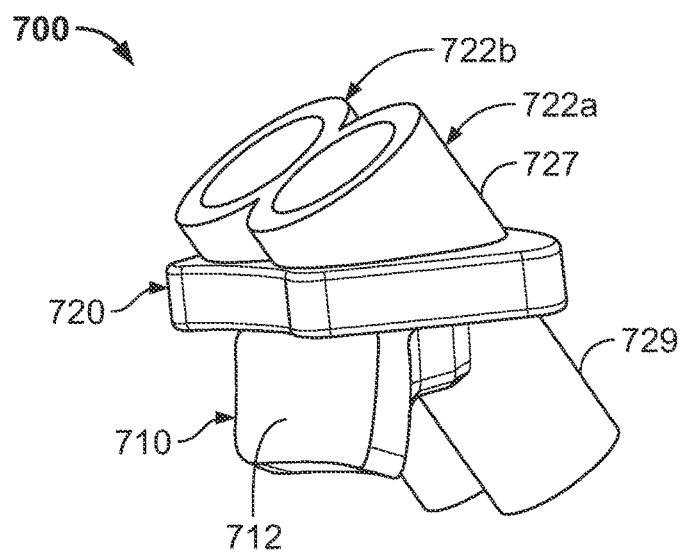
FIG. 11 is a perspective view of an augment according to yet another embodiment of the present disclosure.

FIG. 11 depicts an augment 700 of a still further embodiment of the present disclosure. Augment 700 has a similar configuration to that of guide bodies 508 and 608 and, therefore, may be implanted into a bone defect prepared by one of such guide bodies. Augment 700, like other embodiment disclosed herein, includes a flange 710, bosses 722a-b, and a web 720 connecting flange 710 and bosses 722a-b. However, web 720 extends over flange 710 such that it forms a canopy over flange 710. In this regard, when implanted, concave flange 710 contacts a corresponding convex surface 672 of implant 670 while web 720 rests atop of rim 674 similarly to guide bodies 508 and 608. In addition, bosses 722a-b extend downwardly from web 720 and into corresponding bone openings previously formed by one of the guides described herein. Bosses 722a-b also extend upwardly from web 720 such that bosses 722a-b have a first portion 727 above web 720 and a second portion 729 below web 720. However, in some embodiments, bosses 722a-b may not have a first portion 727 so as to minimize the profile of augment 700 to help prevent impingement and soft tissue irritation.

Figure 12A:
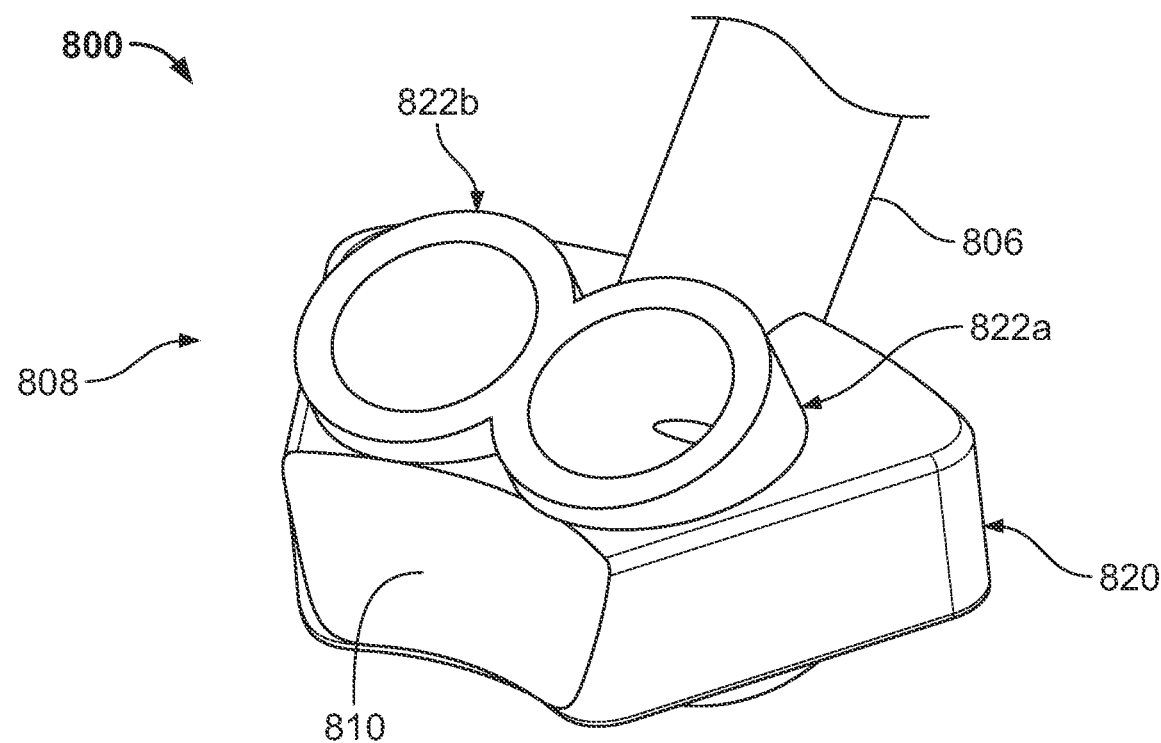
FIG. 12A is a perspective view of a guide according to an additional embodiment of the present disclosure.
Figure 12B:
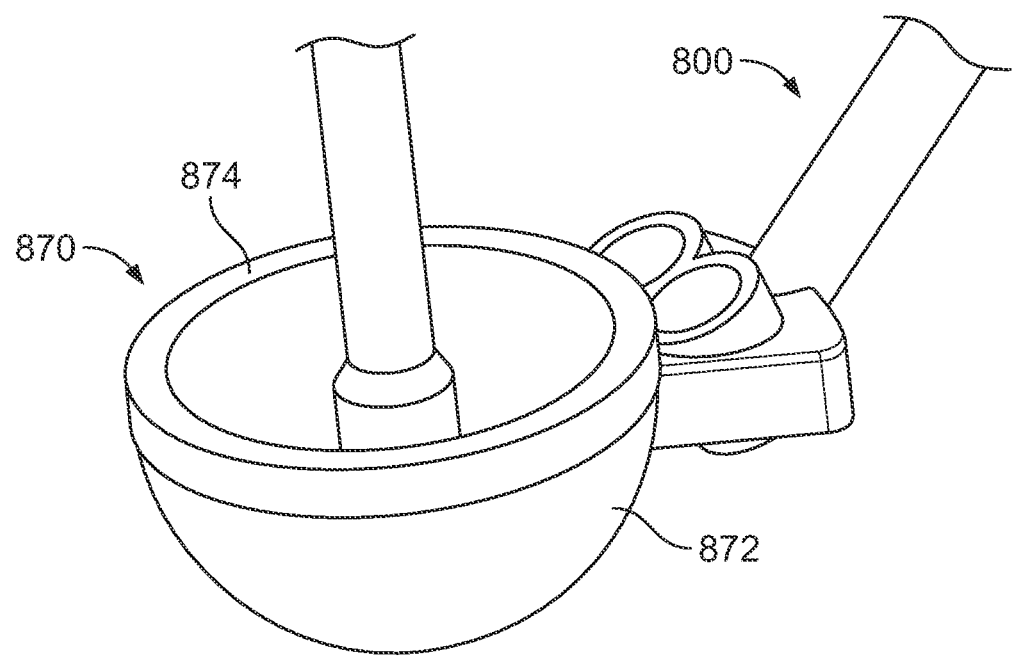
FIG. 12B is a perspective view of the guide of FIG. 12A.

FIGS. 12A and 12B depict a guide 800 according to an even further embodiment of the present disclosure. Guide 800 is similar to guide 140' in that it includes a body 808 that is comprised of a plurality of bosses 822a-b for guiding a drill bit, such as drill bit 180, and a web 820 connecting bosses 822a-b. However, guide 800 is configured to directly contact an outer surface 872 of an acetabular implant 872 without resting on a rim 874 thereof. In this regard, web 820, which encompasses bosses 822a-b, has an indented, concave surface 810 which has a curvature that corresponds to convex surface 872 of acetabular implant 870. In addition, handle 806 is similar to handle 142' in that it connects to guide body 808 at a side thereof. Thus, in use, handle 806 is manipulated to position concave surface 810 against outer convex surface 872 of implant 870 while a cutter or drill bit is driven through bosses 822a-b, as best shown in FIG. 12B.

While the embodiments disclosed herein are discussed relative to an acetabulum, it should be understood that the inventions described herein can be implemented in other locations of the body, such as a glenoid cavity, so as to augment bone defects at those locations. In addition, the embodiments disclosed herein are described as being used in conjunction with a final acetabular cup implant. In this regard, defect preparation and implantation of the augments may be performed after the final acetabular cup implant is implanted into the bone. However, preparation and implantation of the augments described herein can be performed prior to implantation of the final implant. In this regard, a trial implant can be inserted into the bone and then bone preparation is performed in relation to the trial. Alternatively, no trial may be used. Regardless, it is preferable to prepare the bone and implant the augment while the final acetabular implant is in place as it simplifies the procedure and helps ensure the final implant is appropriately supported.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A joint replacement system comprising:
an acetabular cup implant having an outer surface;
a drill bit having a cutting surface;
a guide separately formed from the acetabular cup implant and having a body defining first and second guide openings each adapted to receive the drill bit; and
a void filler prosthesis having an implant facing surface and first and second portions connected to the implant facing surface and each having an outer surface having a geometry corresponding to the cutting surface of the drill bit such that the first and second portions can be received in respective openings in a bone formed by the drill bit,
wherein the first portion includes a first screw opening configured to receive a first bone screw.

2. The system of claim 1, wherein the cutting surface of the drill bit defines a cylinder and the outer surface of each of the first and second portions of the void filler prosthesis is cylindrical.

3. The system of claim 2, wherein a cross-sectional dimension of each of the first and second portions is larger than a cross-section dimension of the drill bit so as to create a press-fit arrangement between the first and second portions and the bone when the first and second portions are received in the openings thereof.

4. The system of claim 1, wherein:
the implant facing surface is concave and an upper surface of the void filler prosthesis intersects the concave surface, the upper surface defining a plane, and
the first screw opening defines a longitudinal axis that intersects the plane at a first angle.

5. The system of claim 4, wherein the first angle is 90 degrees.

6. The system of claim 4, wherein the first angle is 60 to 90 degrees.

7. The system of claim 4, wherein a second screw opening defines a second longitudinal axis parallel to the first longitudinal axis.

8. The system of claim 1, wherein the guide has a flange having a concave surface corresponding the outer surface of the acetabular cup implant, the flange being connected to the body of the guide, the outer surface of the acetabular cup implant being convex.

9. The system of claim 8, wherein the void filler prosthesis includes a flange connected to the first and second portions, the flange having the implant facing surface, the implant facing surface being concave.

10. The system of claim 9, wherein the flange of the guide has a first thickness and the flange of the void filler has a second thickness, the first thickness being greater than the second thickness.

11. The system of claim 1, wherein the void filler prosthesis includes a web connecting the first and second portions and the flange.

* * * * *